United States Patent [19]

Hamilton et al.

[11] Patent Number: 5,577,368
[45] Date of Patent: Nov. 26, 1996

[54] METHOD FOR IMPROVING WEAR RESISTANCE OF POLYMERIC BIOIMPLANTABLE COMPONENTS

[75] Inventors: John V. Hamilton, Foxborough; Mark A. Manasas, South Easton; Timothy M. Flynn, Norton, all of Mass.

[73] Assignee: Johnson & Johnson Professional, Inc., Raynham, Mass.

[21] Appl. No.: 415,733

[22] Filed: Apr. 3, 1995

[51] Int. Cl.$^6$ .................................................. B65B 31/02
[52] U.S. Cl. ............................ 53/432; 53/434; 53/425
[58] Field of Search .......................... 53/432, 510, 434, 53/425, 467, 473; 206/363, 438, 570

[56] References Cited

U.S. PATENT DOCUMENTS

| | | | |
|---|---|---|---|
| 4,336,618 | 6/1982 | Raab | 3/1.913 |
| 4,838,877 | 6/1989 | Massau | 604/272 |
| 5,014,494 | 5/1991 | George | 53/432 |
| 5,137,688 | 8/1992 | DeRudder | 422/22 |
| 5,472,415 | 12/1995 | King et al. | 623/16 |

Primary Examiner—Daniel C. Crane
Assistant Examiner—Ed Tolan
Attorney, Agent, or Firm—William C. Geary, III; Nutter, McClennen & Fish, LLP

[57] ABSTRACT

Wear resistance and oxidation resistance of bioimplantable polymeric parts is improved by packaging the parts within flexible, gas impermeable containers while subjecting the containers and the parts to a relatively high vacuum force. The containers are heat sealed while subjected to the vacuum force such that, upon sealing, hydrostatic pressure is exerted on the part. Following sealing of the packages, the packages and their contents are irradiated to an extent sufficient to sterilize the parts and to promote crosslinking within the part. Alternatively, the same property enhancements can be imparted to polymeric parts by packaging the part within rigid or flexible containers, minimizing the oxygen content within the containers, pressurizing the containers with an inert gas, or with a mixture of hydrogen and an inert gas, to greater than 1.5 atmospheres, and irradiating the part and the container.

35 Claims, 2 Drawing Sheets

METHOD FOR IMPROVING WEAR RESISTANCE OF POLYMERIC BIOIMPLANTABLE COMPONENTS

BACKGROUND OF THE INVENTION

This invention relates to bioimplantable polymeric articles and more particularly to methods of improving the wear resistance and oxidation resistance of such articles.

Advances in biomedical engineering have resulted in numerous polymeric articles which are able to be implanted within the body. Polymeric components are widely used in orthopedic surgery, for example, to form articulation surfaces within artificial joints. Ultrahigh molecular weight polyethylene (UHMWPE) is an example of a polymer that is commonly used to form components of artificial joints.

Among the properties required of bioimplantable polymeric components, particularly those used in artificial joints, are low friction, biocompatibility, and good mechanical properties, including excellent resistance to wear. Such components must also be sterile before implantation within a patient.

Some polymers and medical devices may be adversely affected by heat sterilization, thus such a technique is not widely used. Ethylene oxide sterilization is another technique for sterilizing medical devices, but ethylene oxide can pose health and enviromnental risks that render this method less desirable. As a result, a preferred method of sterilizing many medical devices, including polymeric components, is by exposure to forms of ionizing radiation such as gamma rays, x-rays, or electron beam radiation.

Presently, sterilization by gamma radiation is a preferred method for sterilizing many medical devices, including bioimplantable polymeric components. One potential effect of gamma radiation sterilization is that the gamma rays can initiate chemical reactions within the polymer that can affect the structure, morphology and some mechanical properties of the polymer. During gamma irradiation a variety of chemical species, such as ions, excited molecules, double bonds, oxidation products and free radicals are created within the polymer. Free radicals are believed to be a species generated during gamma radiation that may contribute most to changes in the properties of irradiated polymers.

Once the radicals are formed within a polymer, these species may participate in at least four types of major reactions. The free radicals can undergo a recombination reaction by reacting with hydrogen to eliminate the free radical, by reacting with carbon molecules to create side chains, or both. Free radicals can also undergo a chain scission reaction that results in a decrease in the molecular weight of the polymer, and an increase in the density and crystallinity of the polymer, thus causing some mechanical properties of the polymer to degrade. A crosslinking reaction is another reaction in which the free radicals can participate. Finally, the free radicals may remain within a polymeric material without reacting initially, thus remaining available to react over time as conditions dictate.

The presence of oxygen in polymeric materials and their surrounding environment can contribute to an oxidation reaction in which free radicals and dissolved oxygen react to produce a compound with a carbonyl functional group, resulting in chain scission and the creation of new free radicals. Oxidation can decrease the molecular weight of a polymer (due to chain scission) and contribute to the degradation of its mechanical properties.

Sterilization of polymer components by gamma radiation in air is believed to decrease the wear resistance of polymers due, in part, to oxidation effects. Wear resistance is a key mechanical property for polymeric components that are used in joint prostheses. As a result, a current practice is to sterilize polymeric components in an environment of an inert gas (e.g., argon, helium, nitrogen)to minimize oxidation effects. See, Kurth, M. et al., *"Effects of Radiation Sterilization on UHMW-Polyethylene"* Antec 87, pp. 1193–1197 (1987); Streicher, R. K., *Radiol. Phys. Chem.,* Vol. 31, Nos. 4–6, pp. 693–698 (1988); Streicher, R. M., "Improving UHMWPE by Ionizing Radiation Crosslinking During Sterilization", 17th Annual Meeting of the Society for BioMaterials, p. 181 (1991). Others have used vacuum techniques to help purge an environment of oxygen before conducting gamma radiation sterilization. See, Yong Zhao, et al., *J. Appl. Polymer Sci.,* Vol. 50, pp. 1797–1801 (1993).

Wear resistance is a property of great importance to artificial joint components. Natural friction within a replaced, artificial joint can cause minute particles of debris (e.g., particles from a polymeric component)to become dislodged and to migrate within the joint. This phenomenon of wear debris within artificial joints is a serious problem that can inhibit the proper mechanical functioning of the joint. Wear debris can also lead to osteolysis and bone deterioration. If osteolysis develops around an artificial joint it is usually corrected by surgical removal of the diseased tissue and revision of the artificial joint.

Because excellent wear resistance is a property of such importance for polymeric components used to form artificial joints, it would be advantageous to be able to provide sterilized polymer components that have improved wear resistance.

It is thus an object of the invention to provide methods for increasing the wear resistance of bioimplantable polymeric components. It is also an object to provide sterilization techniques for medical grade implantable polymer components that preserve important properties of the components. A further object is to provide bioimplantable polymeric components that have improved wear resistance and that are less prone to the effects of oxidation. These and other objects will be apparent to one of ordinary skill in the art upon reading the description that follows.

SUMMARY OF THE INVENTION

The invention provides a method for increasing the wear resistance of polymeric parts. The method is particularly well suited to polymeric parts that are biocompatible and that are intended for use as components of artificial joints. A variety of polymeric materials, particularly UHMWPE, can be treated according to the method of the invention to improve wear resistance and to improve oxidation resistance.

According to the method of the invention, one or more manufactured polymeric parts, such as a bioimplantable component, are placed within one or more gas impermeable, flexible packages. Each package has at least one heat sealable opening therein. The packages and the parts therein are then subjected to a relatively strong vacuum force. While under the influence of the vacuum the packages are heat sealed such that after sealing hydrostatic pressure is exerted on the part. Typically, the package is heat sealed shortly after initiating the vacuum, and usually not more than one-half hour after initiating the vacuum. Next, the packages and the parts that are contained within the packages are irradiated for a period of time that is sufficient to sterilize the parts and to promote crosslinking of the polymer that forms the part. Various forms of ionizing energy can be used to sterilize the parts. However, the use of gamma radiation is among the more preferred radiation sterilization techniques.

In another embodiment, manufactured polymeric parts can be placed within a packaging container that is either flexible or rigid. After minimizing or eliminating the oxygen concentration within the container, the container is pressurized to approximately 1.5 to 4 atmospheres with an inert gas, or with a mixture of an inert gas and hydrogen. Thereafter, the parts and the containers are irradiated for a period of time sufficient to sterilize the parts and to promote crosslinking of the polymer that forms the part.

This process has been found to increase the wear resistance of polymeric parts while maintaining other mechanical properties that are important to such parts. An additional benefit of the invention is the improved ability of the polymeric parts to resist oxidation. The resulting sterilized part is characterized by a gel content in the range of about 75 to 100%, indicating high levels of crosslinking within the polymer.

DETAILED DESCRIPTION OF THE INVENTION

Figure 1:
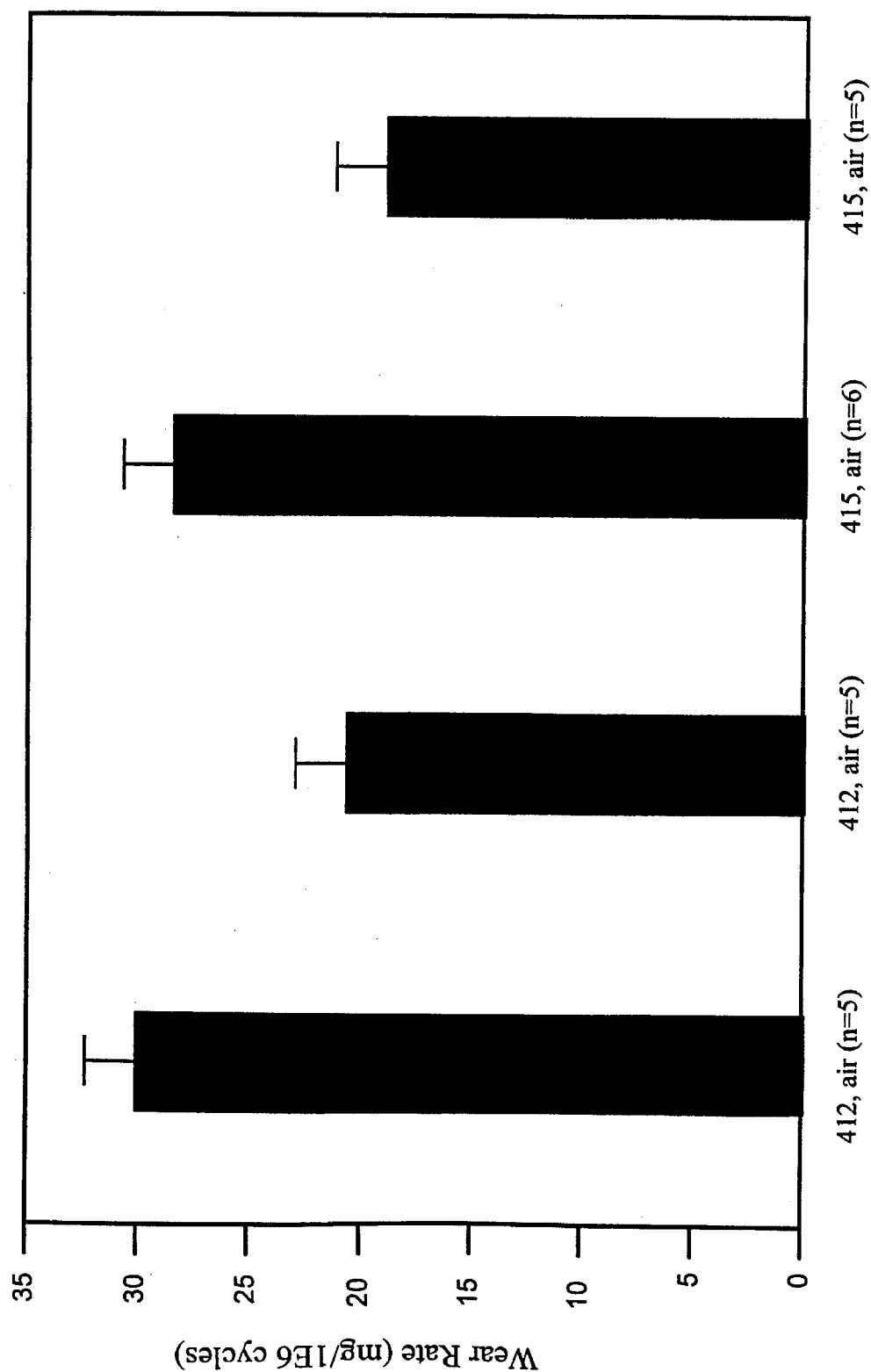
FIG. 1 is a bar graph which plots wear rate (milligrams of weight lost per 1 million cycles) for various samples evaluated in Example 3.

Many polymeric components, such as those comprising UHMWPE, form articulation surfaces for artificial joints. Thus, it is essential that these components possess excellent wear resistance.

The present invention provides a method for improving the wear resistance of manufactured polymeric parts. According to this process the desired polymeric part is first manufactured by known processes, such as compression molding and RAM extrusion. The polymer that forms the part can be low density polyethylene, high density polyethylene, ultrahigh molecular weight polyethylene, polypropylene, polyester, nylon, polyurethane, poly(methylmethacrylate), or other biocompatible polymers typically used in biomedical applications. A preferred polymer is UHMWPE, which is commonly used in a variety of orthopedic implants, such as liners for acetabular shells of artificial hip joints, and as tibial bearing members in artificial knee joints.

In one embodiment, polymeric parts that are to be subjected to the process of the invention are first placed in a flexible package that has a heat sealable opening therein. Preferably, each part is individually packaged, but more than one part can be placed in a single package. The package and the part are then subjected to a relatively high vacuum force while the heat sealable opening remains open. The vacuum force is maintained for approximately 10 seconds to 30 minutes, and preferably for about 30 seconds. Thereafter, the package is heat sealed, while maintaining the vacuum force, rendering the package gas impermeable. Once the package is sealed under vacuum, and following removal of the vacuum force, a hydrostatic pressure in the range of about 7 to 14.7 psi is exerted on the part.

The packaging of the polymeric parts in a heat sealed package under vacuum is effective to reduce pressure within the package and to remove oxygen from the polymeric material and from the environment within the package. Moreover, the hydrostatic pressure which is exerted on the polymeric part is believed to hinder the evolution of hydrogen gas from within the polymer during irradiation.

Following the vacuum heat sealing of the package that contains the polymeric part, the package and the part are irradiated for a period of time that is sufficient to sterilize the part and to initiate crosslinking of polymer chains within the manufactured part. Various acceptable forms of ionizing radiation can be used to effect the sterilization of the part. These radiation forms include gamma rays, x-rays, and electron beam radiation. Currently, the use of gamma radiation is a preferred irradiation technique.

In one aspect of the invention the concentration of hydrogen within the package is in the range of about 30 to 100% by volume. Preferably, the polymeric part is aged in the hydrogen rich gas within the packaging container for a period of time sufficient to enable hydrogen atoms to recombine with any free radicals present within the polymeric parts. Preferably, a suitable aging period is at least about 48 hours following irradiation of the part and the packaging container.

The flexible packaging material within which the polymeric parts are sealed can be selected from among many types of high barrier, flexible packaging material that are commonly used to enclose medical devices. Preferably the packaging material is a multilayered, heat seal peelable packaging material that includes one or more foil layers, various polymer layers and a heat seal coating. Examples of suitable materials are those that include the following layers: polyester film-low density polyethylene-foil-ionomer-heat seal coating. Packaging materials having the following layers can also be used: polyester-low density polyethylene-foil-EAA-linear low density polyethylene-heat seal coating; and polyester-Surlyn-nylon-Surlyn-foil-EAA-linear low density polyethylene-heat seal coating. Suitable packaging materials can be obtained from a variety of sources, including Tolas Health Care Packaging of Feasterville, Pa. The thickness of the packaging material preferably is in the range of about 2 mil to 7 mil.

According to the process of the invention, a relatively strong vacuum force is used which is sufficient to remove all or substantially all oxygen from within the package and the adjacent environment. Preferably, the vacuum force utilized is in the range of approximately 500 to 1013 mbar. A preferred vacuum force is approximately 1000 mbar. Typically, the vacuum force is exerted upon the package and the polymeric material for about 10 seconds to 30 minutes, and preferably for about 30 seconds. While the vacuum force is maintained, the package is heat sealed, rendering it impermeable to gases. Techniques for heat sealing such packaging material while under vacuum force are readily available to those of ordinary skill in the art. Suitable vacuum packaging equipment that is capable of heat sealing packages under vacuum will be known to those of ordinary skill in the art. An example of a suitable vacuum packaging apparatus is a MultiVac A342 apparatus, available from Multivac, Inc. of Kansas City, Mo.

As noted above, the packaged polymeric material preferably is irradiated using gamma radiation. The gamma radiation is administered for a duration and at a dose level which is known to be acceptable for sterilizing medical devices. A dose of approximately 20–60 KGy usually is acceptable, while approximately 35 to 50 KGy is preferred. The irradiation step typically continues for approximately 10 minutes up to about several hours and most preferably for about one to three hours.

In another embodiment, manufactured polymeric parts can be placed in either a rigid or a flexible container. All or most of the oxygen within the container is first evacuated. Next, the container is pressurized with an inert gas (e.g., argon, helium or nitrogen), or with a mixture of an inert gas and hydrogen, to approximately 1.5 to 4 atmospheres. Subsequently, the container and the enclosed polymeric parts are irradiated (using gamma, x-ray, or electron beam radiation) to an extent sufficient to sterilize the parts and to promote crosslinking of the polymer that forms the parts.

A variation of this embodiment can also be utilized by dispensing of the need to evacuate the container. According to this variation, the container is first flushed with a sufficient amount of an inert gas to displace any oxygen, and then the container is pressurized to the desired level with an inert gas, or with a mixture of an inert gas and hydrogen.

A pressurizing gas that is a mixture of an inert gas and hydrogen preferably is hydrogen enriched. The hydrogen enriched inert gas mixture should have a minimum of about $2.2 \times 10^{-3}$ moles of hydrogen gas per gram of polymeric material within the packaging container. In addition, the hydrogen gas within the volume of the packaging container preferably is in the range of about 30% to 95% by volume.

In this embodiment it may also be useful to age the polymeric part following irradiation, for a period of time sufficient to enable hydrogen atoms to recombine with any free radicals within the polymeric parts. A suitable time period preferably is at least about 48 hours.

One of ordinary skill in the art can readily choose a suitable packaging container suitable to be pressurized to 1.5 to 4 atmospheres with an inert gas. Any flexible container that is utilized must, of course have seals strong enough to withstand the pressures to which it will be subjected.

The irradiation of polymers is known to create a variety of chemical species, including free radicals, within the chains of the polymer. Free radicals, as noted above, can participate in a number of reactions. It is believed that the technique of the present invention creates a chemical environment that favors free radicals participating in crosslinking reactions with adjacent polymer chains due to the lack of oxygen available in the system for oxidation reactions. Further, irradiation of the polymer also results in the evolution of hydrogen gas in a quantity that is proportional to the quantity of free radicals created. It is further believed that the use of a technique which packages the polymeric part in a gas impermeable, flexible container, under vacuum, causes hydrostatic pressure to be exerted on the bulk material. The processes of the present invention are believed to be effective to inhibit the diffusion of hydrogen out of the material. In addition, in embodiments where the packaging container is charged to about 1.5 to 4.0 atmospheres with an inert gas, the elevated pressure is believed to inhibit hydrogen diffusion. In other embodiments, the use of a flexible packaging container is believed to enable the developed hydrostatic pressure to hinder diffusion of hydrogen out of the material. These phenomena are believed to help reduce the number of free radicals present within the bulk polymer, thus further reducing the potential for oxidation of the material.

As noted above, the techniques of the present invention are believed to contribute to reducing the amount of hydrogen that diffuses from the bulk polymer, thus maintaining more hydrogen within the polymer. This phenomenon is believed to minimize the extent of chain scission reactions within the polymer since the hydrogen within the polymer evidently decreases the number of free radicals within the polymer available to participate in oxidation reactions by recombining with the free radicals. Following packaging, the concentration of hydrogen within the packaging container is maintained below about $2.2 \times 10^{-5}$ moles/gram, and more preferably at about $1.83 \times 10^{-5}$ moles/gram.

The present invention is also believed to contribute to extensive crosslinking within the polymer. This crosslinking is believed to be responsible for increasing the wear resistance of the polymer since molecular weight is increased and chain scission is less prevalent.

The following examples serve to further illustrate the invention.

EXAMPLES

Example 1

Disks having a diameter of 25.4 mm and a thickness of 12.7 mm were machined from compression molded UHMWPE (GUR 412, available from Poly Hi Solidur/Meditech of Vreden, Germany). The disks were then sealed in flexible, polymer coated/aluminum foil packages under the following conditions. One set of samples was exposed to a 1,000 mbar vacuum prior to sealing of the package, another set of samples was packaged and sealed in air at −300 mbar, and a third set of samples was exposed to vacuum three of 1000 mbar then backfilled with nitrogen to a pressure of −300 mbar prior to sealing. After sealing, all samples were gamma irradiated with a dose of 40 KGy for about 2 hours 20 minutes. Hydrogen gas composition within the packages was measured after sterilization. All measurements were conducted at the same temperature (23° C.) and the pressure inside the bag was equal after sterilization for all samples, i.e., the stiffness of the packages did not contribute to the final package volume. The data obtained are presented in Table 1.

TABLE 1

Hydrogen Gas Measurement

| Sample | Hydrogen Gas (moles/g) | | |
|---|---|---|---|
| | Vacuum | Air | Nitrogen |
| 1 | $1.81 \times 10^{-5}$ | $2.35 \times 10^{-5}$ | $2.40 \times 10^{-5}$ |
| 2 | $1.87 \times 10^{-5}$ | $2.37 \times 10^{-5}$ | $2.39 \times 10^{-5}$ |
| 3 | $1.94 \times 10^{-5}$ | $2.76 \times 10^{-5}$ | $2.30 \times 10^{-5}$ |
| 4 | $1.75 \times 10^{-5}$ | $2.40 \times 10^{-5}$ | — |
| 5 | $1.79 \times 10^{-5}$ | $2.29 \times 10^{-5}$ | — |
| 6 | — | $2.58 \times 10^{-5}$ | — |
| Avg | $1.83 \times 10^{-5}$ | $2.46 \times 10^{-5}$ | $2.36 \times 10^{-5}$ |
| Std. Dev. | $7.29 \times 10^{-7}$ | $1.59 \times 10^{-6}$ | $5.38 \times 10^{-7}$ |

The data of Table 1 indicates that a significantly lesser amount of hydrogen was present within the packages of samples that were processed according to the technique of the present invention. Presumably, more hydrogen remains present within the bulk polymer as the hydrostatic pressure exerted on the polymer hinders the diffusion of hydrogen from the polymer.

Example 2

The gel content of UHMWPE samples was determined according to Method C of ASTM D2765-90 to assess the degree of crosslinking within the polymer. UHMWPE films, 200 microns thick and weighing 0.6 grams, were skived from compression molded GUR 412 UHMWPE. Five films were packaged in air while five films were packaged under a 1000 mbar vacuum in a manner identical to that used in Example 1. After packaging, all the samples were sterilized using gamma radiation at 40 KGy for 2 hours 20 minutes.

The data illustrated in Table 2 indicate that the samples irradiated in air developed no gel. This implies that the number average molecular weight of these samples was reduced from approximately 3,000,000 to less than 500,000. Conversely, the vacuum packaged samples had an average gel content of 87.98%, indicating that extensive crosslinking had occurred within these samples.

TABLE 2

| Sample | Gel Content | |
|---|---|---|
| | Vacuum Packaged | Air Packaged |
| 1 | 88.75 | 0 |
| 2 | 88.33 | 0 |
| 3 | 87.60 | 0 |
| 4 | 86.98 | 0 |
| 5 | 88.25 | 0 |
| Avg | 87.98 | 0 |

The wear resistance of UHMWPE components processed according to the present invention was also evaluated as explained in Examples 3 and 4.

Example 3

Ten hip cup liners were machined from compression molded GUR 412 UHMWPE. Five were packaged under vacuum and five were packaged in air according to the procedure explained in Example 1. Ten other hip cup liners were machined from RAM extruded GUR 415 UHMWPE (available from Poly Hi Solidur of Fort Wayne, Ind.). These samples were tested using a 12-station MATCO/PMMED hip simulator. This simulator is a computer-controlled hydraulic system that produces a biaxial rocking motion of the cups, which is synchronized with the Paul hip loading curb (Paul, J. P., *Proc. Inst. Mech. Eng.*, 181 (3J):8–15, 1966). A body weight of 756N was used, which results in a maximum applied load of 1966 N. All simulator tests were run at 1.1 Hz for at least two million cycles. At seven selected intervals, polyethylene wear was measured on the basis of sample weight loss. All weight loss values were corrected for sample fluid absorption by measuring the weight gains of several untested samples soaked in serum at identical intervals. Wear rates were determined by linear regression of the wear data, beginning after an initial non-linear period (about 100,000 cycles). Total wear was determined by subtracting the final weight for each sample from the initial weight (approximately 6 grams) and correcting for weight gain due to fluid absorption as described above.

Data illustrated in FIG. 1 indicate that the samples packaged and irradiated in air lost approximately 30 milligrams of weight during the test period while samples packaged under vacuum lost only about 16 milligrams of weight during the testing period. Similarly, the RAM extruded UHMWPE samples resulted in a greater weight loss for air packaged samples (about 28 mg) than for vacuum packaged samples (about 17 mg).

The increased weight loss of the air packaged and irradiated samples is indicative of a lower resistance to wear which evidently results from chain scission reactions that take place within the polymer, thus reducing the molecular weight of the polymer.

Example 4

Wear resistance was also evaluated according to another technique in which erosion of a sample caused by revolution of the sample under a metal pin was evaluated. According to this experiment, ten samples of compression molded UHMWPE (GUR 412) disks were obtained together with ten samples of RAM extruded UHMWPE (GUR 415). All samples had the dimensions of 1.25 inches diameter and 0.25 inch thickness. Five samples of each material type were packaged and irradiated in air while five samples of each material type were packaged and irradiated under vacuum, as specified in Example 1.

Following packaging and irradiation, each sample was evaluated for wear resistance by a "Pin-on-Disk" technique. According to this technique, a metal pin having a diameter of approximately 0.25 inch was placed in contact with a surface of each of the test samples. The pin was loaded to 152N while the disk was rotated at 112 rpm. The wear track created by the metal pin was measured at 5 intervals over 2,000,000 cycles using a profilometer to detect volume changes in the UHMWPE sample. A linear regression was performed on the volume changes over the second through the fifth measurements to determine the wear rate.

Figure 2:
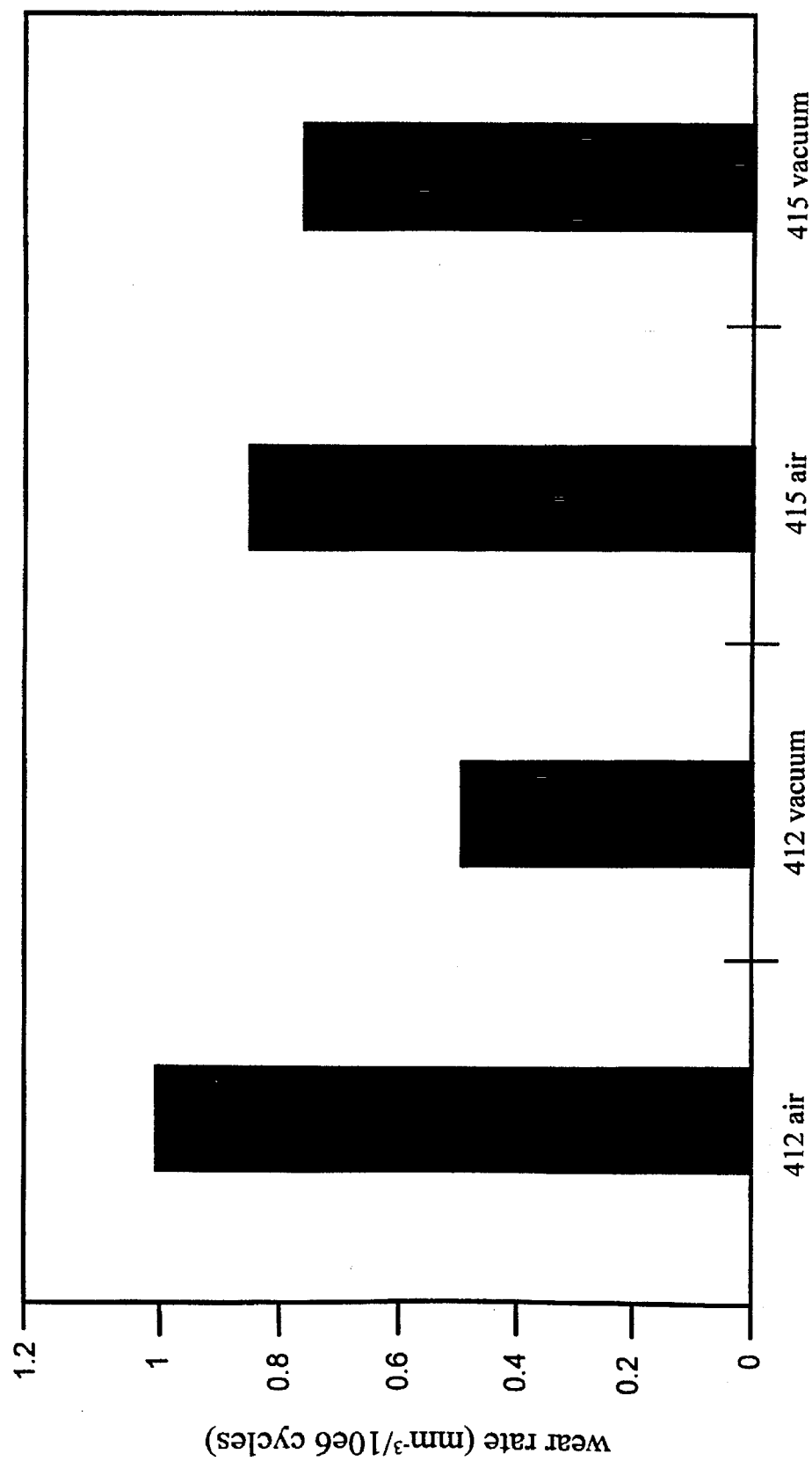
FIG. 2 is a bar graph which plots wear rate ($mm^3$ of wear per 1 million cycles) for various samples evaluated in Example 4.

As illustrated in FIG. 2, the GUR 412 compression molded samples packaged and irradiated in air demonstrated a significantly greater wear rate (1.01 $mm^3$/1,000,000 cycles) than did the samples that were packaged and irradiated under vacuum (0.48 $mm^3$/1,000,000 cycles). The RAM extruded GUR 415 samples demonstrated a less significant reduction in wear rate for the vacuum packaged and irradiated samples. As shown in FIG. 2, the air packaged and irradiated samples demonstrated the wear rate of 0.78 $mm^3$/1,000,000 cycles, while the vacuum packaged and irradiated samples demonstrated a wear rate of 0.74 $mm^3$/1,000,000 cycles.

A second wear criterion was also used in conjunction with this evaluation. Pitting of the wear track was qualitatively evaluated to further assess the effects of wear. Table 3 illustrates this data in which pits present within a wear track were observed.

TABLE 3

| Sample | Track Pitting | |
|---|---|---|
| | Presence of Pits In Sampled Wear Tracks | |
| | Air Sterilized | Vacuum Sterilized |
| GUR 412 | 3 of 6 samples | 0 of 6 samples |
| GUR 415 | 2 of 6 samples | 0 of 6 samples |

The foregoing description of the method of manufacture and the illustrative embodiments is presented to indicate the range of constructions to which the invention applies. Variations in the materials to be used to fabricate polymer samples, vacuum pressures, radiation sources, and the like, will be readily apparent to those having ordinary skill in the art. Such variations are considered to be within the scope of the invention in which patent rights are asserted, as set forth in the claims appended hereto.

The entirely of all publications and/or references noted herein are expressly incorporated by reference herein.

What is claimed is:

1. A method for improving the wear resistance of a polymeric manufactured part, comprising the steps of:
   providing one or more manufactured polymeric parts;
   placing the parts in one or more gas impermeable, flexible packaging containers wherein each container has at least one heat sealable opening therein;
   subjecting the packaging container and the polymeric parts to a vacuum force;
   heat sealing the flexible packaging container while subjected to the vacuum force such that upon sealing of the packaging container hydrostatic pressure is exerted on the part; and
   irradiating the heat sealed packages and the parts for a period of time sufficient to sterilize the parts and to promote crosslinking within the polymer that forms the part;
   the part being characterized by improved resistance to wear and oxidation.

2. The method of claim 1 wherein the vacuum force is sufficient to remove all or substantially all of the oxygen from within the packaging container and the environment adjacent to the packaging container.

3. The method of claim 1 wherein the vacuum force is in the range of about 500–1013 mbar.

4. The method of claim 1 wherein the hydrostatic pressure executed on the part is in the range of about 7 to 14.7 psi.

5. The method of claim 1 wherein any gas contained within the flexible packaging container is characterized by a reduced number of moles of hydrogen.

6. The method of claim 5 wherein the gas within the flexible packaging container has less than about $2.2 \times 10^{-5}$ moles/g of hydrogen.

7. The method of claim 1 wherein the step of irradiating is carried out using gamma, x-ray, or election beam radiation.

8. The method of claim 7 wherein the step of irradiating is carried out until a dose of about 20–60 KGy has been achieved.

9. The method of claim 1 wherein, following the step of irradiating, the part is characterized by a gel content in the range of about 75 to 100% as determined by Method C of ASTM D2765-90.

10. The method of claim 1 wherein the flexible packaging container is manufactured of a metal foil that is surrounded by one or more layers of a polymer film.

11. The method of claim 1 wherein the polymeric part is made from a polymer selected from the group consisting of low density polyethylene, high density polyethylene, ultrahigh molecular weight polyethylene, polypropylene, polyester, nylon, polyurethane, and poly(methylmethacrylate).

12. The method of claim 1 wherein the polymeric part is made from an ultrahigh molecular weight polyethylene having a number average molecular weight greater than about 1.0 million.

13. The method of claim 12 wherein the polymeric part is manufactured by a compression molding process.

14. The method of claim 12 wherein the polymeric part is manufactured by a RAM extrusion process.

15. The method of claim 1 wherein, following the step of irradiating, the method further comprises the step of
   aging the polymeric parts within a hydrogen enriched atmosphere of the packaging container for a period of time sufficient to enable hydrogen atoms to recombine with free radicals within the polymer.

16. The method of claims 15 wherein the hydrogen rich atmosphere within the container has approximately 30% to 100% hydrogen by volume.

17. The method of claim 15 wherein the polymeric parts are aged for at least 48 hours.

18. A method for improving the wear resistance of a polymeric manufactured part, comprising the steps of:
   providing one or more manufactured polymeric parts;
   placing the parts in one or more sealable, gas impermeable packaging containers;
   removing all or substantially all of the oxygen from within the packaging container;
   pressurizing the packaging containers with an inert gas at a pressure greater than about 1.5 to 4.0 atmospheres;
   irradiating the pressurized containers and the polymeric parts for a period of time sufficient to sterilize the parts and to promote crosslinking within the polymer that forms the part;
   the part being characterized by improved resistance to wear and oxidation.

19. The method of claim 18 wherein the step of minimizing the oxygen concentration within the packaging container is effected by flushing the container with an inert gas.

20. The method of claim 18 wherein the step of minimizing the oxygen concentration within packaging containers is effected by applying a vacuum force to the container.

21. The method of claim 18 wherein the inert gas is selected from the group consisting of argon, helium, and nitrogen.

22. The method of claim 18 wherein the packaging container is rigid.

23. The method of claim 18 wherein the packaging container is flexible.

24. The method of claim 18 wherein the step of irradiating is carried out using gamma, x-ray, or electron beam radiation.

25. The method of claim 24 wherein the step of irradiating is carried out until a dose of about 20–60 KGy has been achieved.

26. A method for improving the wear resistance of a polymeric manufactured part, comprising the steps of:
   providing one or more manufactured polymeric parts;
   placing the parts in one or more sealable, gas impermeable packaging containers;
   removing all or substantially all of the oxygen from within the packaging container;
   pressurizing the packaging containers with a mixture of hydrogen gas and an inert gas at a pressure greater than about 1.5 atmospheres;
   irradiating the pressurized containers and the polymeric parts for a period of time sufficient to sterilize the parts and to promote crosslinking within the polymer that forms the part;
   aging the part within the atmosphere of the irradiated packaging container for a period of time sufficient for hydrogen atoms to recombine with free radicals within the part;
   the part being characterized by improved resistance to wear and oxidation.

27. The method of claim 26 wherein the mixture of hydrogen gas and an inert gas is characterized by a minimum of about $2.2 \times 10^{-3}$ moles of hydrogen gas per gram of polymeric material within the packaging container and a volumetric concentration of hydrogen within the container in the range of about 30% to 95%.

28. The method of claim 26 wherein the part is aged within the packaging container for at least about 48 hours.

29. The method of claim 26 wherein the step of minimizing the oxygen concentration within the packaging container is effected by flushing the container with an inert gas.

30. The method of claim 26 wherein the step of minimizing the oxygen concentration within packaging containers is effected by applying a vacuum force to the container.

31. The method of claim 26 wherein the inert gas is selected from the group consisting of argon, helium, and nitrogen.

32. The method of claim 26 wherein the packaging container is rigid.

33. The method of claim 26 wherein the packaging container is flexible.

34. The method of claim 26 wherein the step of irradiating is carried out using gamma, x-ray, or electron beam radiation.

35. The method of claim 34 wherein the step of irradiating is carried out until a dose of about 20–60 KGy has been achieved.

* * * * *

UNITED STATES PATENT AND TRADEMARK OFFICE
CERTIFICATE OF CORRECTION

PATENT NO. : 5,577,368
DATED : November 26, 1996
INVENTOR(S) : John V. Hamilton, Mark A. Manasas, and Timothy M. Flynn It is certified that error appears in the above-indentified patent and that said Letters Patent is hereby corrected as shown below:

In Column 6, line 29, please replace "three" with --force--.

Signed and Sealed this

Twenty-seventh Day of January, 1998

Attest:

BRUCE LEHMAN

Attesting Officer

Commissioner of Patents and Trademarks